United States Patent
Mewissen-Scholberg et al.

(10) Patent No.: US 7,641,678 B2
(45) Date of Patent: Jan. 5, 2010

(54) TANNING APPARATUS

(75) Inventors: Jan Alfons Catharina Mewissen-Scholberg, Middelkerke (BE); Anne Meijer, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 473 days.

(21) Appl. No.: 10/573,740

(22) PCT Filed: Sep. 29, 2004

(86) PCT No.: PCT/IB2004/051912

§ 371 (c)(1),
(2), (4) Date: Mar. 28, 2006

(87) PCT Pub. No.: WO2005/034165

PCT Pub. Date: Apr. 14, 2005

(65) Prior Publication Data

US 2007/0035253 A1    Feb. 15, 2007

(30) Foreign Application Priority Data

Oct. 2, 2003 (EP) .................. 03103665

(51) Int. Cl.
*A61N 5/06* (2006.01)
*H05B 37/02* (2006.01)

(52) U.S. Cl. .............. 607/94; 315/159; 315/152; 315/153; 315/154; 315/312; 250/494.1

(58) Field of Classification Search ............ 607/94; 315/159, 49; 250/494.1
See application file for complete search history.

(56) References Cited

U.S. PATENT DOCUMENTS

| 2,092,363 | A | * | 9/1937 | Hans et al. | 313/44 |
| 2,344,122 | A | * | 3/1944 | Bay et al. | 315/49 |
| 3,048,741 | A | * | 8/1962 | Thouret | 315/49 |
| 4,100,462 | A | * | 7/1978 | McLellan | 315/179 |
| 4,268,780 | A | * | 5/1981 | Roche et al. | 315/179 |
| 4,283,661 | A | * | 8/1981 | Doty | 315/360 |
| 4,287,454 | A | * | 9/1981 | Feuersanger et al. | 315/178 |
| 4,287,554 | A | * | 9/1981 | Wolff | 362/218 |
| 4,298,005 | A | * | 11/1981 | Mutzhas | 607/94 |

(Continued)

FOREIGN PATENT DOCUMENTS

EP    0375011 A1    6/1990

(Continued)

OTHER PUBLICATIONS

Menezes, Salatiel et al. Non-Coherent Near Infrared Radiation Protects Normal Dermal Fibroblasts from Solar Ultraviolet Toxicity. The Society for Investigative Dermatology, Inc. 1998.*

(Continued)

*Primary Examiner*—Roy D Gibson
*Assistant Examiner*—Kaitlyn E Helling

(57) ABSTRACT

A tanning apparatus for radiation treatment for personal care includes at least one gas discharge UV lamp, at least one ballast connected in series with said at least one gas discharge lamp, and at least one incandescent lamp separate from the gas discharge lamp or lamps. The weight of the inductive ballast is reduced in that the incandescent lamp(s) is included in the ballast or ballasts(s).

16 Claims, 2 Drawing Sheets

U.S. PATENT DOCUMENTS

| | | | | |
|---|---|---|---|---|
| 4,309,616 | A * | 1/1982 | Wolff | 250/494.1 |
| 4,340,843 | A * | 7/1982 | Anderson | 315/205 |
| 4,350,929 | A * | 9/1982 | Katoogi | 315/49 |
| 4,356,433 | A * | 10/1982 | Linden | 315/308 |
| 4,367,432 | A * | 1/1983 | Glenny et al. | 315/49 |
| 4,382,210 | A | 5/1983 | Buhrer | |
| 4,438,369 | A * | 3/1984 | Hicks et al. | 315/49 |
| 4,494,041 | A * | 1/1985 | Roche et al. | 315/49 |
| 4,536,680 | A * | 8/1985 | Roberts | 315/49 |
| 4,751,435 | A | 6/1988 | Roche et al. | |
| 4,888,526 | A * | 12/1989 | Nilssen | 315/324 |
| 6,661,177 | B2 * | 12/2003 | Luijks et al. | 315/60 |
| 6,717,164 | B2 * | 4/2004 | Ullrich et al. | 250/504 R |
| 7,196,478 | B2 * | 3/2007 | Dijkstra | 315/209 R |
| 7,201,767 | B2 * | 4/2007 | Bhullar | 607/94 |
| 2002/0047529 | A1 | 4/2002 | Luijks et al. | |
| 2005/0007032 | A1 * | 1/2005 | Dijkstra | 315/291 |

FOREIGN PATENT DOCUMENTS

| | | |
|---|---|---|
| EP | 375011 A1 * | 6/1990 |
| GB | 2050090 A | 12/1980 |
| GB | 2146185 A | 4/1985 |
| WO | WO 2007091194 A1 * | 8/2007 |

OTHER PUBLICATIONS

Salatiel Menezes, et al: Non-Coherent Near Infrared Radiation Protects Normal Human Dermal Fibroblasts from Solar Ultraviolet Toxicity, vol. 111, No. 4 Oct. 1998, Antagonism Between Solar IR and UV, The Journal of Investigative Dermatology, pp. 629-633.

* cited by examiner

1

TANNING APPARATUS

This is a national stage entry of PCT/IB04/51912 filed Sep. 29, 2004 which claims priority to EPO 3103665.0 filed Oct. 10, 2003.

This invention relates to a tanning apparatus for irradiating human skin for tanning.

More specifically, this invention relates to a tanning apparatus for radiation treatment for personal care, comprising at least one gas discharge ultraviolet (UV) lamp, at least one ballast connected in series with said at least one gas discharge lamp, and at least one incandescent lamp separate from the at least one gas discharge lamp.

Such apparatuses are known from practice, for instance in the form of the PHILIPS HB975B tanning apparatus. This apparatus includes UV lamps and reflectors for irradiating the skin of a person positioned in the radiation emitted by the apparatus. An inductive coil ballast is connected in series with the gas discharge lamp for stabilizing the current through the gas discharge lamp. The incandescent lamp is an infrared (IR) lamp, which provides the possibility of irradiating the body with IR radiation for relaxation. At least under certain conditions, IR radiation may also be used in the case of various symptoms such as muscular pain or stiffness. In general, it is desired to reduce the weight of such an apparatus, to facilitate its handling, and to allow a lighter construction without impairing durability.

As such, the use of a tungsten filament as the ballast connected in series with the arc tube is well known in the art. However, the tungsten filament ballasts are integrated in self-ballasted discharge lamps for the purpose of operating the lamps directly from a conventional electric power supply source without the use of external transformers, inductive reactors, or other similar external means for ballasting and starting and for providing some initial illumination directly after startup until the discharge lamp has been started.

For instance, U.S. Pat. No. 3,048,741 discloses a self-ballasted arc lamp in which a high-pressure mercury vapor lamp comprising an auxiliary electrode for igniting the arc in the high-pressure mercury vapor lamp and a tungsten filament forming the ballast in series with the discharge lamp. The tungsten filament is arranged in a chamber separate from the arc chamber containing mercury vapor to avoid blackening of the bulb surrounding the arc chamber by material originating from the tungsten filament during its operating life of 12,000 to 15,000 hours. However, in tanning systems, it is generally advised to replace the UV lamp after about 750 hours, because the intensity of UV radiation gradually reduces after such an operating time. Replacement would then take place long before the end of the operating life of the tungsten filament. Furthermore, instant illumination after a switch-on of power to the UV source is of little importance for a tanning system, because the purpose of the UV source is to generate UV radiation for tanning and not illumination for vision.

It is an object of the invention to provide a tanning system with a UV source and an incandescent radiation source that is lighter than the known systems.

According to the invention, this object is achieved by including the incandescent radiation lamp or lamps in the ballast or ballasts. By including the separate incandescent radiation lamps in the ballast for the gas discharge UV lamps, the need of heavy inductive windings for ballasting the gas discharge UV lamps is avoided or at least lighter windings may be applied, so that the weight of the apparatus is reduced.

Particular embodiments of the invention are set forth in the dependent claims.

Figure 1:
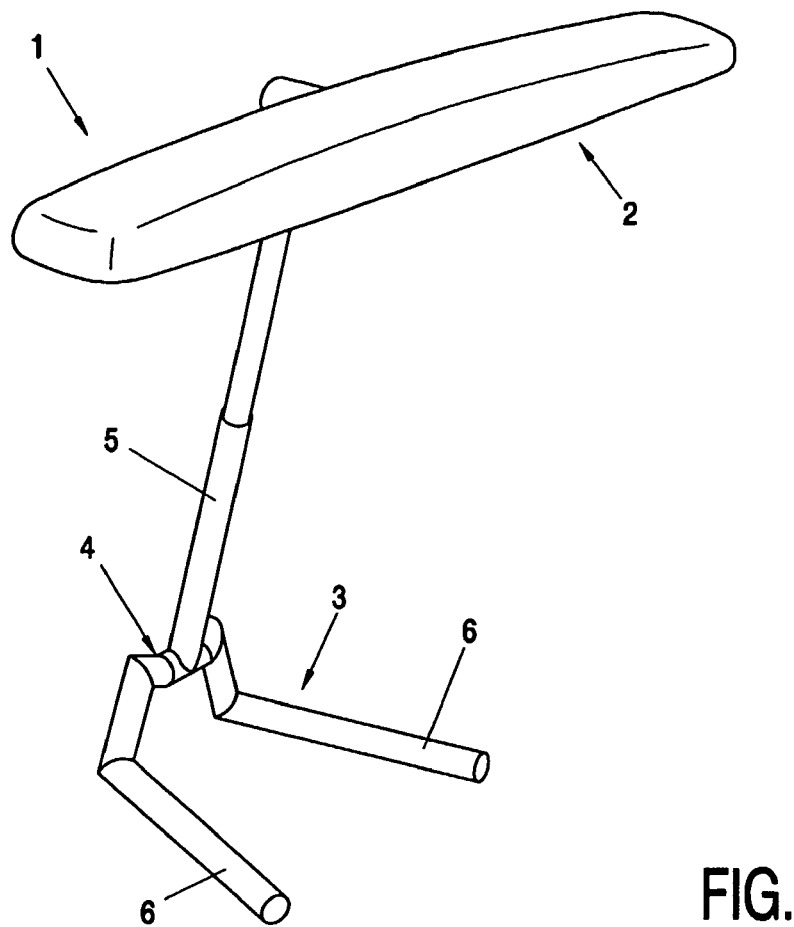
FIG. 1 is a perspective view of a tanning apparatus according to the invention.

FIG. 1 shows an example of a tanning apparatus according to the invention. The tanning apparatus according to the present example is collapsible. However, the invention may also be embodied in a non-collapsible tanning apparatus.

The apparatus according to this example includes a lamp housing 1 in which lamps are arranged. The lamp housing 1 has irradiating windows in its downward-facing side 2, through which windows radiation is directed from the lamps, partially via reflectors, to a person to be tanned positioned under the lamp housing 1. It is observed that the invention may also be embodied in tanning apparatuses intended or suitable for irradiating in a generally horizontal direction the body or a portion thereof, such as the face only, of a person seated or standing in front of the irradiating window. Transparent filter panels are positioned in the windows. Depending on the type of lamps used, the transparent panels may also be of a type that does not provide any substantial filtering effect, or the windows may be completely open or provided with safety grids, only for preventing the user from touching or hitting the lamps.

A telescopically extendable post 5 extends upwardly from a support 3 and carries the housing 1. The support 3 has two feet 6 that project from a coupling 4, to which the post 5 is also mounted, underneath the lamp housing 1. The feet are journaled to the coupling 4 so as to be pivotable about axes extending obliquely to the post 5 into a configuration extending closely along and approximately parallel to the post 5. This allows the stand for carrying the lamp housing 1 to be folded into a very compact configuration. In the operational condition, the feet 6 are arranged such that they project under a bed or other support for the person to be tanned. The heavier the housing 1 and the assemblies arranged therein, the heavier and/or larger the feet 6 need to be to prevent the tanning apparatus from falling over.

Figure 2:
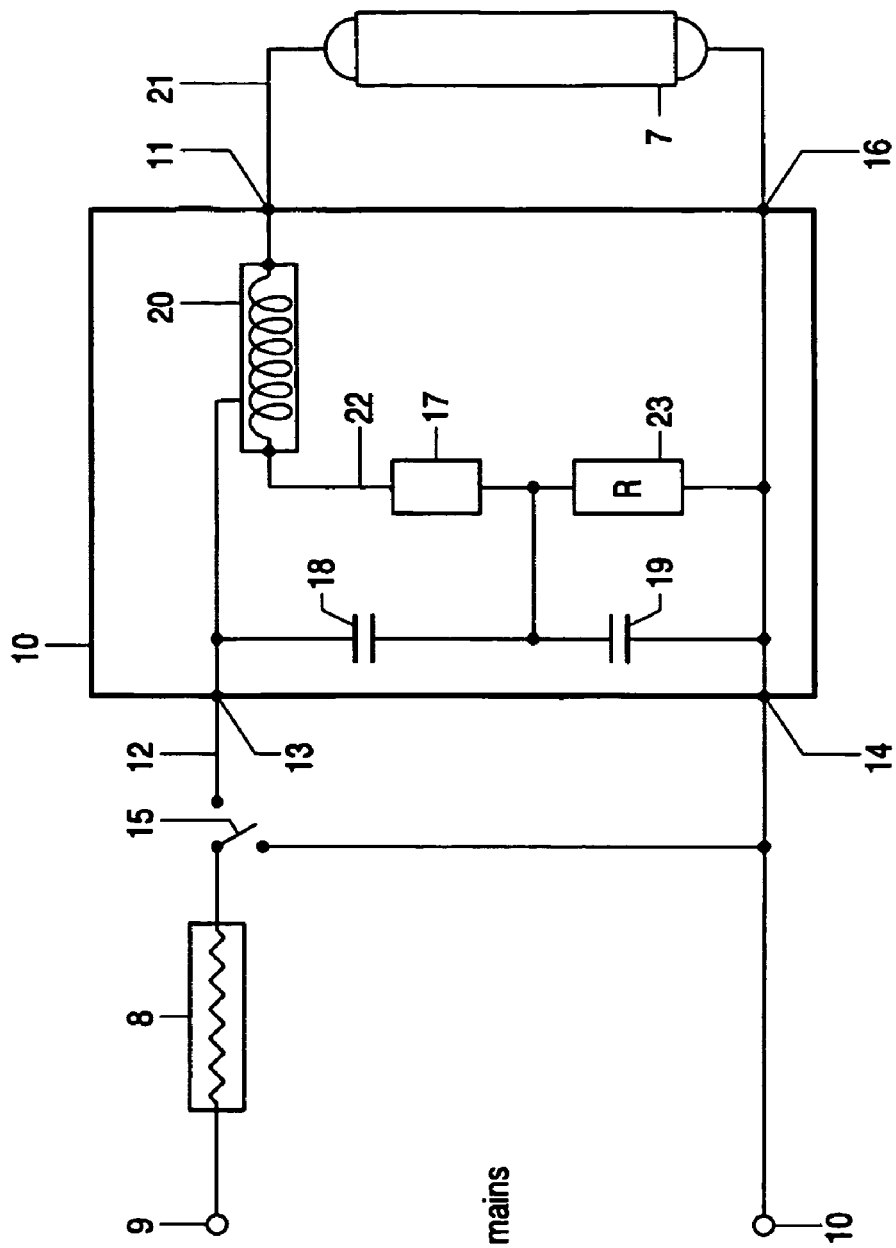
FIG. 2 is a circuit diagram of a tanning apparatus according to the invention.

In FIG. 2, for the sake of simplicity, a circuit including the lamps and for power supply is schematically illustrated and described for one UV lamp and one incandescent lamp. The tanning apparatus according to FIG. 1 is equipped with two UV lamps and two incandescent lamps, but other combinations of numbers of lamps are equally conceivable. According to the present example, the incandescent lamps are IR lamps. However, in addition or as an alternative, lamps that do not specifically irradiate IR radiation may be used as well, for instance where a high intensity of visual light is acceptable or desired, for instance for the treatment of winter depressions in regions with long periods of darkness during the winter.

The illustrative circuit of FIG. 2 includes a gas discharge UV lamp 7 and a ballast 8 connected in series with the gas discharge lamp 7 for stabilizing the current through the gas discharge lamp 7 after start-up. The circuit further includes contacts 9, 10 connected to the mains. The ballast 8 is formed by a resistance in the form of the incandescent IR lamp, which is separate from the gas discharge lamp 7. The ballast may include one or more additional other components, such as an inductive coil or control circuitry. By providing an incandescent lamp for performing at least a substantial part of the ballast function, a comparatively light weight ballast is provided and the need of a, usually heavy and costly, inductive coil for controlling the current through the gas discharge lamp is obviated.

Furthermore, the lightweight ballast can be mounted to the housing 1 without causing the apparatus to tip over too easily when in the operative condition. This in turn allows the support for the lamp housing 1 to be of an extremely slender design, requiring very little storage room, as is illustrated by the example shown in FIG. 1. Another advantage of the ballast being mounted to the housing 1 is that all or most electrical components can be assembled in a single subassembly. The lamp housing 1 then does not need to be joined to the stand until at or briefly before the time of packaging of the tanning apparatus. Preferably, the incandescent lamp forming the ballast is mounted in the lamp housing, so that that the lamp housing 1 also shields the incandescent lamp to reduce the risk of damaging the incandescent lamp.

For obtaining a lightweight tanning apparatus, it is also advantageous if compact and lightweight UV lamps, such as high intensity discharge (HID) lamps and, more specifically, metal halide radiators are used. HID lamps are often referred to as high-pressure lamps. Also medium-pressure metal halide radiators fall within the term HID lamps. According to the present example, the gas discharge UV lamps are medium-pressure metal halide radiators with iron and cobalt additives, emitting ozone-free radiation mainly between 280 and 400 nm. Such lamps are commercially available.

If HID lamps are to produce UV radiation efficiently, the power input must be much greater than the heat conduction from the discharge. Power input to a HID lamp is therefore usually close to or above 20 watts per centimeter of discharge length.

Lamps of the above-identified HID and/or high or medium pressure type that are not equipped with an auxiliary electrode require a starting circuit that is arranged for generating a peak voltage across the gas discharge lamp, so that the gas-discharge arc in the lamp is started up.

To achieve starting up of the gas-discharge arc in a lamp connected to a power supply circuit in which an incandescent lamp is included in the ballast, without requiring a gas discharge lamp provided with an auxiliary electrode for starting and without complicated electronic control circuitry, the circuit further includes an igniter circuit 10 for generating a voltage peak for starting up an arc through the gas discharge lamp 7. The igniter circuit 10 has a contact 11 for outputting a voltage pulse that is applied to the gas discharge UV lamp 7. The contact 11 for outputting a voltage pulse is separate from a contact 13 connecting the igniter circuit 10 to the mains via the IR lamp 8. Also the connection 21 via which the contact 11 for outputting a voltage pulse is connected to the gas discharge lamp 7 is separate from the connection 12 between the igniter circuit 10 and the mains via the IR lamp 8. A third contact 14 of the igniter circuit 10 is connected to the other pole 10 of the mains, in series with a contact 16 and the gas discharge lamp 7. The fact that the contact 11 via which the voltage peak for starting up the gas discharge lamp 7 is outputted is connected to the gas discharge lamp 7 via a contact separate from the IR lamp 8 ensures that the voltage peak is transferred to the gas discharge lamp 7 and not through the IR lamp 8, which would cause disturbances in the mains via contact 9.

The igniter circuit 10 includes a current pulse generator 17. An output line 22 connects the pulse generator 17 to a transformer 20 of the igniter circuit 10. First and second capacitors 18, 19 are connected in parallel with the gas discharge lamp 7, and the connection between the capacitors 18 and 19, which are connected in series with each other, is also connected to a connection between the current pulse generator 17 and a resistor 23 in series with the current pulse generator 17. When power is applied to the circuit of FIG. 2 and the arc in the lamp 7 has not been instated, the voltage across the capacitor 18 reaches a break-over voltage of the current pulse generator 17, causing the current pulse generator 17 to switch to an on-state and to produce a pulse of current through the primary of the transformer 20. In response to the current pulse through the primary of the transformer 20, the transformer generates a high-voltage pulse via the voltage output contact 11, the connection 21, and the lamp 7. This voltage pulse causes the lamp 7 to be ignited, so that a current starts to flow through the gas discharge lamp 7. When, after the lamp 7 has started, the voltage across the capacitor 18 has dropped back below the break-over voltage, the current pulse generator 17 returns to its off-state.

Since the igniter circuit 10 is connected to the gas discharge lamp 7 via an output conductor 21 separate from the input conductor 12, disturbance of the mains is counteracted. The inductive coil of the transformer 20 shields the mains from disturbance by the voltage peak, in spite of the absence of an inductive coil, or at least any significant inductive coil, in the ballast 8.

The circuit further includes a switch 15 connected between the power supply circuit and the IR lamp 8, for connecting the IR lamp 8 to the power supply separately from the UV lamp 7. This allows the user to enjoy the warmth of IR radiation also without being exposed to UV radiation (which can be endured without causing a sunburn for a limited period of time only).

The IR radiation output of the IR lamp 8 is higher when it operates without the UV lamp 7 connected in series than with the UV lamp 7 connected in series. This is advantageous, because more warmth is required to achieve a pleasant, comfortable feeling in the absence of the UV radiation and of the IR radiation that is additionally emitted by the UV lamp 7 when active.

Figure 3:
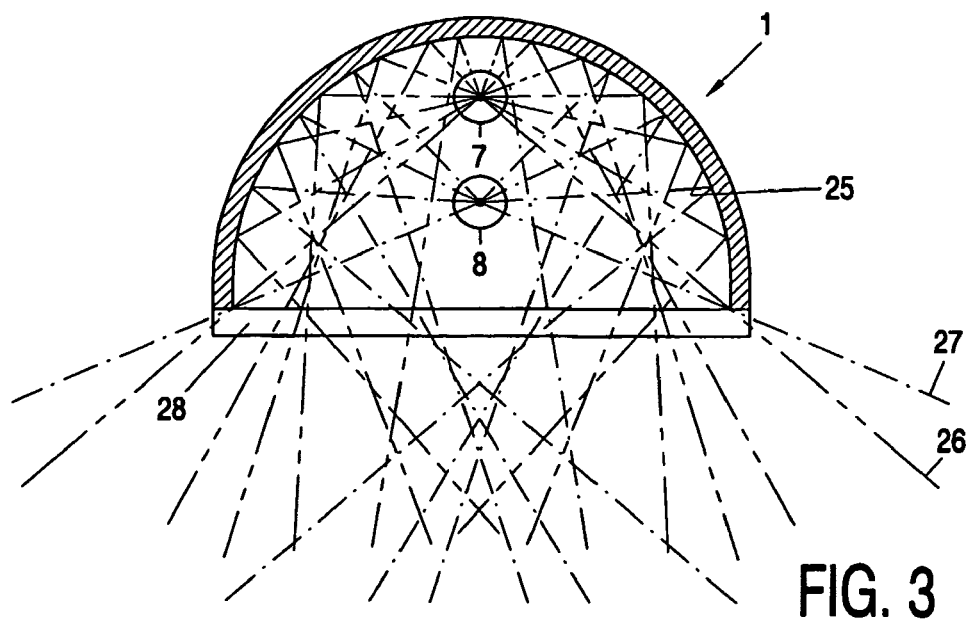
FIG. 3 is a central cross-sectional view of a lamp housing of a tanning apparatus according to the invention.

The housing 1 shown in FIG. 1 is schematically illustrated in more detail in FIG. 3. The UV lamp 7 and the IR lamp 8 are arranged in front of a reflector 25. The reflector 25 concentrates UV radiation into a UV radiation beam 26 towards an area to be irradiated, in which area the skin to be tanned is to be positioned. The IR lamp 8 is arranged for radiating a portion of its infrared radiation 27 in a direction other than towards the UV-irradiated area. Accordingly, a portion of the IR radiation is not radiated towards the skin of the person in the UV radiation beam 26. This allows the use of UV lamps of relatively high power (thus achieving a quick tanning effect) without heating up the skin too much by the IR radiation, of which the power is proportional to the power of the UV lamps.

According to the present example, keeping a portion of the IR radiation away from the user in the UV radiation beam 26 is achieved in a simple manner, by positioning the IR lamp in such a position relative to the reflector 25 that the IR radiation beam 27 encloses a wider angle than does the UV radiation beam 26. It is, however, also possible to keep a portion of the IR radiation away from the user in other manners, for instance by positioning the IR lamp behind a shield and allowing some of the IR radiation to pass through a window in a side of the housing facing away from the user.

Since the reflector 25 is arranged for bundling both UV radiation and IR radiation, a very compact and light construction is achieved.

The UV radiation lamp 7 produces a comparatively large quantity of effective radiation with a wavelength in the range <320 nm (UVB), which radiation is mainly responsible for tanning of the skin, and a comparatively small quantity of effective radiation with a wavelength in the range from 320 to 400 nm (UVA). On the other hand, it is desired to provide UV radiation that also contains a reasonable amount of UVA radiation. As is known in the art, this is achieved by providing a lamp of a higher power than would be allowed in view of the UVB intensity and to provide a filter 28 shielding the user from the reflector 25 and the lamps 7, 8. This filter 28 filters out a substantial portion of the UVB radiation, such that the effective radiation intensity thereof does not exceed the value of 0.15 W/m$^2$ (European standard EN 60335-2-27) in the irradiation plane, even if the power of the lamp is such that a substantial UVA radiation intensity is achieved. Another reason for using relatively high-power lamps is that otherwise the (undressed) user would get too cold to be comfortable.

However, in combination with the warmth provided by the IR radiation from the IR radiator 8, a lower power level of the UV radiator 7 may be selected while still radiating sufficient energy to the user to avoid the user feeling cold. Therefore, the power of the lamps is preferably selected to be 25 to 50% lower than usual, and the UVB radiation intensity limit will then be reached if the filter 28 allows at least 15% and preferably about 15-25% of UVB radiation to pass. Such a filter typically has a transmittance at 305 nm of at least 15%.

The UVA radiation intensity will then accordingly be 25 to 50% lower as well, but even at half the power the total UV radiation intensity is still about 80% of the intensity at the conventional, higher power. The time of a single tanning treatment (of which the duration is determined by the allowable exposure of the skin to UV radiation per treatment) at half the power is then only about 5 minutes longer.

To reduce absorption of IR radiation by the filter 28 (glass with a good IR transmission rate) and/or by glass of the IR lamp, the IR lamp 8 is a near-IR lamp. Preferably, a further filter is provided for shielding the user from at least a portion of the visible light emitted by the IR lamp.

The invention claimed is:

1. A tanning apparatus for radiation treatment for personal care comprising at least one gas discharge UV lamp, at least one ballast connected in series with said at least one gas discharge UV lamp, and at least one incandescent lamp separate from the at least one gas discharge lamp, wherein said at least one incandescent lamp is included in said at least one ballast and is operable without said at least one gas discharge UV lamp, said at least one incandescent lamp and said at least one gas discharge UV lamp being included in a reflector.

2. The tanning apparatus according to claim 1, further including at least one igniter circuit for generating a voltage peak for starting up an arc through the at least one gas discharge lamp, wherein said igniter circuit is connected to said incandescent lamp and to said gas discharge UV lamp via an input conductor, and wherein said igniter circuit is connected for outputting a current pulse to the at least one gas discharge lamp via an output conductor separate from said input conductor.

3. The tanning apparatus according to claim 2, wherein the at least one gas discharge UV lamp is a high intensity discharge lamp.

4. The tanning apparatus according to claim 3, wherein the at least one high intensity discharge lamp is a metal halide lamp.

5. The tanning apparatus according to claim 1, wherein the reflector is arranged for concentrating UV radiation into a UV radiation beam towards an irradiated area, wherein said at least one incandescent lamp is arranged for radiating at least a portion of radiation generated thereby in a direction other than towards said irradiated area.

6. The tanning apparatus according to claim 5, further including at least one reflector arranged for concentrating radiation from said incandescent lamp into an incandescent radiation beam, wherein said incandescent radiation beam encloses a wider angle than does said UV radiation beam.

7. The tanning apparatus according to claim 6, wherein said reflector or at least one of said reflectors is arranged for concentrating both UV radiation and incandescent radiation into a beam.

8. The tanning apparatus according to claim 1, further including a switching structure comprising at least one switch connected between a power supply circuit and said at least one incandescent lamp for connecting said at least one incandescent lamp to said power supply separately from said at least one UV lamp.

9. The tanning apparatus according to claim 1, including at least one filter for filtering UV radiation from said gas discharge UV lamp, said filter being adapted for transmitting at least 15% of UV radiation below 320 nm wavelength.

10. The tanning apparatus according to claim 1, including at least one filter for filtering UV radiation from said gas discharge UV lamp, said filter being adapted for transmitting at least 15% of UV radiation at 305 nm wavelength.

11. The tanning apparatus according to claim 1, wherein said incandescent lamp is mounted to a housing in which the UV discharge lamp is arranged.

12. The tanning apparatus according to claim 1, wherein said incandescent lamp is an IR lamp.

13. The tanning apparatus according to claim 12, wherein said IR lamp is a near-IR lamp.

14. The tanning apparatus of claim 1, wherein said at least one incandescent lamp provides higher radiation when operated without said at least one gas discharge UV lamp than when said at least one incandescent lamp operates with said at least one gas discharge UV lamp.

15. The tanning apparatus of claim 1, further comprising a switch having a first state and a second state, wherein in said first state power is provided to only said at least one incandescent lamp, and in said second state power is provided to said at least one gas discharge UV lamp through said at least one incandescent lamp.

16. The tanning apparatus of claim 1, wherein said at least one incandescent lamp and said at least one gas discharge UV lamp are independently replaceable.

* * * * *